United States Patent
Sano et al.

(10) Patent No.: US 10,315,974 B2
(45) Date of Patent: Jun. 11, 2019

(54) CRYSTALLINE MALTITOL POWDER LESS PRONE TO CONSOLIDATION AND METHOD FOR PRODUCTION THEREOF

(71) Applicant: MITSUBISHI SHOJI FOODTECH CO., LTD., Tokyo (JP)

(72) Inventors: Chihaya Sano, Shizuoka (JP); Takashi Noguchi, Shizuoka (JP); Tohru Nemoto, Shizuoka (JP); Koshiro Shimazu, Shizuoka (JP)

(73) Assignee: MITSUBISHI SHOJI FOODTECH CO., LTD., Tokyo (JP)

( * ) Notice: Subject to any disclaimer, the term of this patent is extended or adjusted under 35 U.S.C. 154(b) by 333 days.

(21) Appl. No.: 14/963,394

(22) Filed: Dec. 9, 2015

(65) Prior Publication Data

US 2016/0214916 A1 Jul. 28, 2016

Related U.S. Application Data

(63) Continuation of application No. 11/574,071, filed as application No. PCT/JP2005/015162 on Aug. 19, 2005.

(30) Foreign Application Priority Data

Aug. 25, 2004 (JP) ................. 2004-245104

(51) Int. Cl.
| | |
|---|---|
| C07C 29/76 | (2006.01) |
| C07H 15/04 | (2006.01) |
| G01N 11/00 | (2006.01) |
| G01N 33/02 | (2006.01) |
| A61K 9/14 | (2006.01) |
| A23L 29/30 | (2016.01) |
| A23L 27/30 | (2016.01) |

(52) U.S. Cl.
CPC .............. *C07C 29/76* (2013.01); *A23L 27/34* (2016.08); *A23L 29/37* (2016.08); *A61K 9/146* (2013.01); *C07H 15/04* (2013.01); *G01N 11/00* (2013.01); *G01N 33/02* (2013.01); *A23V 2002/00* (2013.01); *C07B 2200/13* (2013.01)

(58) Field of Classification Search
None
See application file for complete search history.

(56) References Cited

U.S. PATENT DOCUMENTS

| | | |
|---|---|---|
| 3,918,986 A | 11/1975 | Hiraiwa |
| 4,408,041 A | 10/1983 | Hirao et al. |
| 4,717,765 A | 1/1988 | Hirao et al. |
| 4,789,559 A | 12/1988 | Hirao et al. |
| 4,846,139 A | 7/1989 | Devos et al. |
| 5,304,388 A | 4/1994 | Ueno et al. |
| 5,873,943 A | 2/1999 | Magara et al. |
| 2001/0006956 A1 | 7/2001 | Leleu et al. |
| 2009/0114214 A1 | 5/2009 | Barata et al. |
| 2009/0163700 A1 | 6/2009 | Boit et al. |

FOREIGN PATENT DOCUMENTS

| | | |
|---|---|---|
| EP | 0 461 886 A1 | 12/1991 |
| EP | 0 735 042 | 10/1996 |
| EP | 0 937 733 | 8/1999 |
| JP | 51-113813 | 10/1976 |
| JP | 51-128441 | 11/1976 |
| JP | 56-133229 | 10/1981 |
| JP | 63-2439 | 1/1988 |
| JP | 04-045836 | 2/1992 |
| JP | 2000-229668 | 8/2000 |
| JP | 2002-253167 | 9/2002 |
| WO | WO2004067595 A2 * | 8/2004 |

OTHER PUBLICATIONS

Watano, S. et al., Journal of Chemical Engineering of Japan, "Drying of Granules in Agitation Fluidized Bed", 1998, vol. 31, No. 6, pp. 908-913 (Year: 1998).*
Fluid Air Inc. Product line, available at http://www.fluidairinc.com/fluid_bed_systems.html; retrieved Apr. 12, 2018, two pages (Year: 2018).*
English machine translation of EP0735042 obtained from the European Patent Office (1996) [online] retrieved Feb. 28, 2012. Retrieved from the internet <http://worldwide.espacenet.com>.
"Lesys Crystalline Maltitol" from Mitsubishi Shoji Foodtech Co., Ltd. [online] Retrieved Feb. 28, 2012, Retrieved from <http://www.lesys-maltitol.com/production.html>.
Mitsubishi Shoji Foodtech Co., Ltd., Supplementary European Search Report for European Patent Application No. EP 05772593.9, dated Apr. 23, 2012, 4 pages.

(Continued)

*Primary Examiner* — Shaojia A Jiang
*Assistant Examiner* — Bahar Craigo
(74) *Attorney, Agent, or Firm* — Kenneth H. Sonnenfeld; Margaret B. Brivanlou; King & Spalding LLP

(57) ABSTRACT

[Object] It is intended to provide a crystalline maltitol powder less prone to consolidation, which is free from the formation of a lump during delivery or storage thereof, does not require pulverization or re-classification in use, is easy to handle in transfer, package opening, addition or mixing to another food material, and so on, and allows for automated transportation and so on.
[Means for solving the object] The crystalline maltitol powder less prone to consolidation is obtained by charging crystalline or powdery maltitol into a shelf type dryer, a tunnel-type dryer, a cylindrical container, or the like and subjecting the equipment or container to a treatment wherein an air having a temperature of 30 to 33° C. and a relative humidity of 5% is allowed to flow into the equipment or container from one side thereof and withdrawn out of the other side thereof at a space velocity of 11 to 12 for consecutive 24 hours. Even when the relative humidity is 45%, the crystalline maltitol powder less prone to consolidation can be obtained by combining therewith other conditions such as an appropriate space velocity of the feed of air and an appropriate treatment duration.

6 Claims, 1 Drawing Sheet

(56) References Cited

OTHER PUBLICATIONS

Roquette Certificate, Maltisorb P200—Maltitol, Factory Lestrem/Barnier Eric, Dec. 12, 2003, 3 pages.

Charles G. Hill, Jr, The University of Wisconsin, "An Introduction to Chemical Engineering Kinetics & Reactor Design", 1977, pp. 254-257.

Yoon et al., Enhancement of $H_2$ Production by Combination with $CO_2$ Absorption in Steam Methane Reforming in Bench Scale, Received Apr. 9, 2007, Accepted May 30, 2007, J. Ind. Eng. Chem., Vo. 13, No. 5, (2007) pp. 842-849.

John W. Robinson, Jr., Catalyst Emissions Education Program, A Scheduled Series from Catalytic Combustion's "Catalyst 101", pp. 1-19, Catalytic Combustion Quality Catalysts Since 1950, www.CatalyticCombustion.com.

* cited by examiner

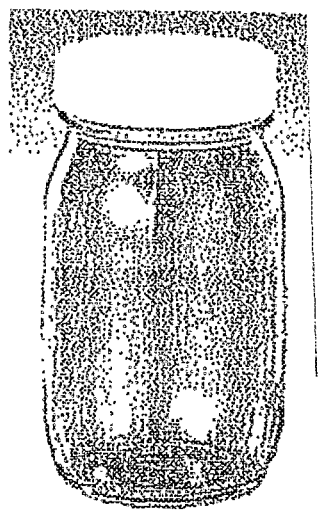

CRYSTALLINE MALTITOL POWDER LESS PRONE TO CONSOLIDATION AND METHOD FOR PRODUCTION THEREOF

TECHNICAL FIELD

The present invention relates to a crystalline maltitol powder useful as a sweetener, in particular, to a crystalline maltitol powder less prone to consolidation during delivery or storage, and a method for production thereof.

BACKGROUND ART

Maltitol is one of sugar alcohols and is a useful substance widely used in the fields of foods, drugs, cosmetics, and so on.

The existence of powder products of maltitol has been known since around 1974 (see e.g., Patent Document 1). However, maltitol powders known at that time were free from crystals and became sticky immediately on exposure to air by absorbing moistures due to their exceedingly strong hygroscopicity. Therefore, they could not serve as commodities that endure delivery or storage.

The existence of crystals among various sugar alcohols has been known since a long time ago for sorbitol, mannitol, and the like. However, the crystals of maltitol have been found as recently as 1981.

Practicable maltitol powder products have been put into circulation since 1981 after their crystal products having low hygroscopicity were found. The physical properties thereof and a method for production thereof have been introduced as anhydrous maltitol crystals (see e.g., Patent Document 2).

As described above, practical crystalline maltitol powders have a shorter history of being put into circulation compared to other sugar alcohols. However, they are currently used in wider fields than those for other sugar alcohols, including chewing gum, chocolate, baked goods (e.g., cookies), and other foods or drinks, because their quality and intensity of sweetness are exceedingly similar sugar.

Powder products of sugar alcohols are generally packaged, stored, and delivered in a resin (e.g., polyethylene) inner bag combined with a kraft bag or in a resin inner bag combined with a corrugated cardboard carton. Currently commercially available crystalline maltitol powders adopt also the former or latter packaging form.

However, most of sugar alcohol powder products are highly hygroscopic as compared with other powder products and tend to cause so-called consolidation, in which powder particles form a cluster.

In general, consolidation seen in powdery products means in a broad sense that individual powder particles adhere to each other for some reason such as natural phenomena or artificial manipulation and thereby form a cluster.

In this case, the phenomena include moisture absorption and air drying, and the manipulation includes addition of water, forced drying, compression, and sintering. In a narrow sense, consolidation refers, in many cases, to a formation of cluster via moistures caused by repetitive moisture absorption and drying, after adherence stage between powder particles by liquid film bridging or the like resulting form adsorption of water molecules thereto.

Crystalline maltitol powder products are rated as having low hygroscopicity as compared with other sugar alcohol powder products. Nevertheless, it is known that crystalline maltitol powder products generate consolidation during delivery or storage, as they have hygroscopicity similarly with other sugar alcohol powder products.

The consolidation state of the crystalline maltitol powder products seems to be variously influenced by storage conditions and so on of the products. The consolidation level thereof also varies from a low level of consolidation in which a cluster is easily reduced into powders with a light touch of hand and recovers powder flowability to a high level of consolidation in which a cluster is not reduced even by a strong impact.

In the present specification, consolidation level refers to consolidation of powder particles, specifically, to the presence or absence of consolidated matter and to the strength of the consolidated matter.

Crystalline maltitol powders consolidated during storage or delivery already lose the feature of powder. Such powders not only exceedingly hinder handling in works such as transfer, package opening, pulverization, and dissolution but arise problems including reducing work efficiency, failure of automated equipment and thus difficult to use in a variety of applications. Therefore, their commercial values are drastically reduced.

Various attempts have been made so far in order to solve objects including high hygroscopicity and ease of consolidation presented by sugar alcohol powder products.

These attempts include, for example, (1) a method wherein other components such as silicon dioxide, calcium aluminosilicate, and a surfactant are added and mixed into a sugar alcohol powder in order to prevent consolidation, and (2) a method wherein a desiccating agent such as silica gel is put into a small bag, which is in turn placed between a outer packaging material and an inner bag or in the interior of the inner bag, or a hygroscopic material is confined between a outer material and inner material of an outer packaging material designed to take a double structure.

However, when the former method (1) is applied, the resulting powder presents a problem of cloudiness when dissolved in water. Moreover, there were problems including: impurities mixed into a product largely impair the commercial value thereof; quality of taste, which is an important factor for crystalline maltitol powder products, is changed; and use of a product is limited as additives cannot be used in some fields. Therefore, crystalline maltitol powders obtained by applying this method are absent in the market.

Alternatively, the method (2) was applied in some cases such as crystalline xylitol powder products. However, there were problems including: a desiccating agent might be mixed accidentally into a product in large-scale production; and cost is increased because the method requires adding a hygroscopic material and carefully taking it out in use of the product. Therefore, the adoption of the method is confined to a small number of crystalline xylitol powder products. The method was not adopted for crystalline maltitol powders and is not distributed.

Furthermore, (3) a method for preventing consolidation of powdery sorbitol, characterized by mixing powdery sorbitol in a mixer at a temperature from 50° C. up to melting temperature for 10 or more minutes has been proposed as an attempt to solve the conventional objects (see e.g., Patent Document 3). However, this method requires an operation of mechanically mixing the powder and therefore requires new equipment in addition to conventional production equipment. Moreover, it presents problems such as crush of powder particles cannot be avoided.

Moreover, the above-mentioned method is intended to prevent a phenomenon specific to sorbitol in which "hair-like crystals chronologically develop in a vertical direction from surfaces of sorbitol powder particles and mutually intertwine". The phenomenon in which hair-like crystals chronologically develop in a vertical direction from surfaces of powder particles has not been observed for crystalline maltitol powders. There have been no cases in which the method was adopted for crystalline maltitol powders based on the premise that such an event would occur.

Patent Document 1: Japanese Laid-Open Patent Application No. 51-113813

Patent Document 2: Japanese Patent Publication No. 63-2439

Patent Document 3: Japanese Laid-Open Patent Application No. 56-133229

DISCLOSURE OF THE INVENTION

Object to be Solved by the Present Invention

For currently distributed crystalline maltitol powders, conventional problems of consolidation during delivery or storage have not been solved, and satisfactory products have not been obtained yet. An object of the present invention is to provide a crystalline maltitol powder less prone to consolidation, which shows excellent powder flowability during delivery or storage and to provide a method for production thereof.

Means to Solve the Object

A general method for producing crystalline maltitol typically includes a method wherein a maltitol aqueous solution is crystallized and subjected to a molasses separation step such as centrifugation to obtain a crystal containing approximately 3% by weight of moisture, and this crystal is then adjusted to a moisture content of approximately 0.1% by weight following a drying step at approximately 70° C. and filled into a packaging material. A crystalline maltitol powder product thus produced is often consolidated during storage or delivery.

For conventional measures against moisture absorption and consolidation, it was deemed to be preferred that moistures should be removed from powder products to the extent possible, and the powder products should be filled into packages, in a dried state, as much as possible. Thus, the conventional measures were carried out in this way while the problems of moisture absorption and occurrence of consolidation were not solved even though the powder products were handled with much care.

According to the experiments of the present inventors, crystalline maltitol powders having small moisture content as 0.3% by weight or less were consolidated in some cases, while crystalline maltitol powders having slightly larger moisture content were not consolidated in other cases.

From these results, it was deduced that the consolidation is not always caused by the amount of a moisture in a crystalline maltitol powder and is largely influenced by a difference in moisture content between the surface of a crystalline maltitol powder and the inside of the powder, and by the state of the powder surface.

Based on these findings, the present inventors have conducted diligent studies on the physical and chemical properties and consolidation phenomenon of a crystalline maltitol powder. As a result, instead of reducing a moisture content in powder particles as conventionally, the present inventors treated the powder with various methods such as a method involving taking into consideration a balance between a moisture content in the inside of powder particles and a moisture content in the surface of the powder particles or a balance between a moisture content in the inside or surface of powder particles and a moisture content in an atmosphere and a method involving stabilizing the surface of the powder, after a production method generally performed, as described in the above, or during the drying stage of the general production method. Thus, the present inventors have successfully obtained a crystalline maltitol powder showing a consolidation level of a score of 0.6 or lower in a result of a consolidation level assay designed by them. Thus, the present invention has been completed.

Specifically, a first aspect of the present invention relates to a crystalline maltitol powder less prone to consolidation, wherein the score of the crystalline maltitol powder of consolidation level measured by a consolidation level assay shown below is 0.6 or lower.

Consolidation Level Assay:

50 g of a sample crystalline maltitol powder is charged into a commercially available sample bottle (hereinafter, also simply referred to as bottle; commonly called a mayonnaise bottle or UM sample bottle; 150 ml in maximum capacity, 4.1 cm in mouth inside diameter, 5.5 cm in shell diameter, and 9.5 cm in overall height) under an environment having a relative humidity of 50% and a temperature of 20° C. The bottle is tightly stoppered with accompanying polyethylene inner and polypropylene outer lids, and a vinyl tape is further provided thereon to seal the boundary between the lids and the bottle. The above-mentioned sample bottle (see FIG. 1) can be purchased from, for example, Uezono Youki Co., Ltd., and the above-mentioned vinyl tape can be exemplified preferably by a 19-mm-wide vinyl chloride Eslon tape manufactured by Sekisui Chemical Co., Ltd.

Next, the sealed bottle is charged into a chamber equipped with a temperature control and evaluated according to the following judgment criteria (1) to (3) after a lapse of 20 days of storage at a temperature of 20° C. and 40° C. alternately repeated at intervals of 12 hours. Five identical samples are prepared for the evaluation, and an average value of test results of these five samples is used as the degree of consolidation in the present assay method of degree of consolidation.

(1) A score of 0 is given when the sample powder wholly flows toward the bottle mouth and thereby exhibits flowability without attaching onto the inside bottom of the sample bottle or slightly attaches onto the inside bottom of the sample bottle but flows toward the bottle mouth and thereby exhibits flowability, on the way of tilting the sample bottle containing the sample at an angle of 90 degrees (leveling horizontally the sample bottle kept in an upright position) without giving an impact thereto;

(2) a score of 1 is given when the sample powder neither flows nor shows flowability by tilting the sample bottle at an angle of 90 degrees but flows toward the bottle mouth on the way of or within 1 minute after further tilting the bottle at an angle of 180 degrees; and (3) a score of 2 is given when the sample powder does not flow toward the bottle mouth even after a lapse of 1 minute after tilting the sample bottle at an angle of 180 degrees.

A second aspect of the present invention relates to a crystalline maltitol powder less prone to consolidation according to the first aspect of the present invention, wherein the score of the crystalline maltitol powder of consolidation level measured by a consolidation level assay shown below is 0.4 or lower.

A third aspect of the present invention relates to a crystalline maltitol powder less prone to consolidation according to the second aspect of the present invention, wherein the score of the crystalline maltitol powder of consolidation level measured by a consolidation level assay shown below is 0.2 or lower.

A fourth aspect of the present invention relates to a crystalline maltitol powder less prone to consolidation according to any one of the first to third aspects of the present invention, wherein a moisture content of the crystalline maltitol is 0.2% or less by weight, and a maltitol content measured by high-performance liquid chromatography is 98% or more by weight per solid content.

A fifth aspect of the present invention relates to the crystalline maltitol powder less prone to consolidation according to any one of the first to fourth aspects of the present invention, wherein 90% or more of the powder is a powder that has passed through a JIS sieve with a mesh size of 0.50 mm (which corresponds to a 32-mesh Tyler screen).

A sixth aspect of the present invention relates to a method for producing a crystalline maltitol powder less prone to consolidation, comprising the step of bringing an air having a temperature of 20 to 50° C. and a relative humidity of 5 to 50% into contact at a space velocity [=SV] of 2 to 15 ($h^{-1}$) for 5 to 50 hours with a crystalline maltitol powder having a score exceeding 0.6 in degree of consolidation measured by an assay method of degree of consolidation shown below, and thereby converting the crystalline maltitol powder to a crystalline maltitol powder having a score of 0.6 or lower in the degree of consolidation.

Assay Method of Degree of Consolidation:

50 g of a sample crystalline maltitol powder is charged into a commercially available sample bottle (hereinafter, also simply referred to as bottle; commonly called a mayonnaise bottle or UM sample bottle; 150 ml in maximum capacity, 4.1 cm in mouth inside diameter, 5.5 cm in shell diameter, and 9.5 cm in overall height) under an environment having a relative humidity of 50% and a temperature of 20° C. The bottle is tightly stoppered with accompanying polyethylene inner and polypropylene outer lids, and a vinyl tape is further provided thereon to seal the boundary between the lids and the bottle. The above-mentioned sample bottle (see FIG. 1) can be purchased from, for example, Uezono Youki Co., Ltd., and the above-mentioned vinyl tape can be exemplified preferably by a 19-mm-wide vinyl chloride Eslon tape manufactured by Sekisui Chemical Co., Ltd.

Next, the sealed bottle is charged into a chamber equipped with a temperature control and evaluated according to the following judgment criteria (1) to (3) after a lapse of 20 days of storage at a temperature of 20° C. and 40° C. alternately repeated at intervals of 12 hours. Five identical samples are prepared for the evaluation, and an average value of test results of these five samples is used as the degree of consolidation in the present assay method of degree of consolidation.

(1) A score of 0 is given when the sample powder wholly flows toward the bottle mouth and thereby exhibits flowability without attaching onto the inside bottom of the sample bottle or slightly attaches onto the inside bottom of the sample bottle but flows toward the bottle mouth and thereby exhibits flowability, on the way of tilting the sample bottle containing the sample at an angle of 90 degrees (leveling horizontally the sample bottle kept in an upright position) without giving an impact thereto;

(2) a score of 1 is given when the sample powder neither flows nor shows flowability by tilting the sample bottle at an angle of 90 degrees but flows toward the bottle mouth on the way of or within 1 minute after further tilting the bottle at an angle of 180 degrees; and (3) a score of 2 is given when the sample powder does not flow toward the bottle mouth even after a lapse of 1 minute after tilting the sample bottle at an angle of 180 degrees.

A seventh aspect of the present invention relates to a method for producing a crystalline maltitol powder less prone to consolidation according to the sixth aspect of the present invention, comprising the step of bringing an air having a temperature of 25 to 42° C. and a relative humidity of 8 to 45% into contact at a space velocity [=SV] of 3 to 14 ($h^{-1}$) for 8 to 48 hours with a crystalline maltitol powder having a score exceeding 0.6 in degree of consolidation measured by an assay method of degree of consolidation, and thereby converting the crystalline maltitol powder to a crystalline maltitol powder having a score of 0.6 or lower in the degree of consolidation.

An eighth aspect of the present invention relates to a method for producing a crystalline maltitol powder less prone to consolidation according to the sixth or seventh aspect of the present invention, wherein the air brought into contact has a temperature of 28 to 33° C., and a crystalline maltitol powder having a score of 0.4 or lower in the degree of consolidation measured by the assay method of degree of consolidation is obtained.

A ninth aspect of the present invention relates to a method for producing a crystalline maltitol powder less prone to consolidation according to the eighth aspect of the present invention, wherein a crystalline maltitol powder having a score of 0.2 or lower in the degree of consolidation measured by the assay method of degree of consolidation is obtained.

A tenth aspect of the present invention relates to a method for producing a crystalline maltitol powder less prone to consolidation according to any one of the sixth to ninth aspects of the present invention, wherein a crystalline maltitol powder having a score of 0.6 or lower in the degree of consolidation measured by the assay method of degree of consolidation has a moisture content of 0.2% or less by weight and a maltitol content of 98% or more by weight per solid content.

An eleventh aspect of the present invention relates to a method for producing a crystalline maltitol powder less prone to consolidation according to any one of the sixth to tenth aspects of the present invention, wherein 90% or more by weight of the crystalline maltitol powder having a score of 0.6 or lower in the degree of consolidation measured by the assay method of degree of consolidation is a powder that has passed through a JIS sieve with a mesh size of 0.50 mm.

Effect of the Present Invention

The crystalline maltitol powder of the present invention is less prone to consolidation during storage or delivery and has stable powder properties for a long period. Therefore, the crystalline maltitol powder does not require new pulverization or drying in transfer, package opening, and use, is applicable to automatic powder transportation by air or the like, and has advantages such as easy automation and exceedingly easy handling because of hardly causing inconvenience such as clogging of powder.

BRIEF DESCRIPTION OF DRAWINGS

FIG. 1 is a diagram showing a commercially available sample bottle used in an assay method of degree of consolidation according to the present invention.

BEST MODE OF CARRYING OUT THE INVENTION

A crystalline maltitol powder less prone to consolidation of the present invention is not particularly limited as long as it is a crystalline maltitol powder less prone to consolidation having a score of 0.6 or lower in degree of consolidation measured by the above-described assay method of degree of consolidation designed by the present inventors (hereinafter, referred to as "the present assay method of degree of consolidation"). The crystalline maltitol powder of the present invention can be exemplified particularly preferably by a crystalline maltitol powder having a score of 0.4 or lower, more preferably 0.2 or lower, and particularly preferably 0, in the degree of consolidation measured by the present assay method of degree of consolidation.

A crystalline maltitol powder that may be adopted as a raw material as a crystalline maltitol powder less prone to consolidation of the present invention can be exemplified specifically by currently distributed commercially available "crystalline maltitol" and "maltitol crystals containing molasses". The "crystalline maltitol" is obtained as a crystalline maltitol powder product by adding or generating a seed crystal for crystallization to a high-purity maltitol aqueous solution and achieving separation between crystals and molasses from the maltitol slurry thus formed, followed by drying and classification according to need. The "maltitol crystal containing molasses" is obtained as a crystalline maltitol powder product according to a method comprising spray-drying a maltitol aqueous solution with high purity and a high concentration in the presence or absence of a seed crystal, or by adding or generating a seed crystal to a maltitol aqueous solution and extruding maltitol magma generated by cooling and kneading from a nozzle, followed by drying, pulverization, and classification steps as required. The "crystalline maltitol" is often differentiated more clearly in "property of less prone to consolidation" from conventional products than the "maltitol crystal containing molasses" and is therefore preferable as a crystalline maltitol powder less prone to consolidation of the present invention.

The crystalline maltitol powder less prone to consolidation of the present invention is characterized by enduring environments during delivery or storage for a longer period than ever before and maintaining powder flowability, and by being less prone to consolidation even in a torture test under severe conditions such as the present assay method of degree of consolidation. The crystalline maltitol powder of the present invention does not require new pulverization or drying step in transfer, packaging opening, and use, and it is applicable to automatic powder transportation by air or the like. Further, it has advantages such as easy handling because of hardly causing inconvenience such as the clogging of the powder.

Various modified methods are possible as a method for producing the crystalline maltitol powder less prone to consolidation of the present invention. Examples thereof include a method comprising the step of charging a crystalline maltitol powder into a shelf type dryer, a tunnel-type dryer, a cylindrical container (column), or the like and subjecting the equipment or container to a contact treatment wherein an air having a temperature of 20 to 50° C., preferably 25 to 42° C., more preferably 28 to 33° C., and a relative humidity of 5 to 50%, preferably 8 to 48%, is allowed to flow into the equipment or container from one side thereof and withdrawn out of the other side thereof at a space velocity [=SV] of 2 to 15 ($h^{-1}$), preferably 3 to 14 ($h^{-1}$), for consecutive 5 to 50 hours, and preferably for consecutive 8 to 48 hours. It has been found that a crystalline maltitol powder less prone to consolidation can be obtained not only when the relative humidity is low but also when the relative humidity is high by combining therewith other conditions such as an appropriate space velocity of the feed of air and an appropriate treatment duration.

A totally unexpected finding was that even the treatment using an air particularly having a high relative humidity such as 45% gave a crystalline maltitol powder having previously unknown properties and showing a score of 0.6 or lower, preferably 0.4 or lower, more preferably 0.2 or lower, particularly preferably 0, in a result of the present assay method of degree of consolidation.

If a crystalline maltitol powder less prone to consolidation of the present invention has a moisture content of approximately 0.3% or less byweight , the crystalline maltitol powder can become an excellent product further less prone to consolidation during normal storage or delivery. In a preferred embodiment of the present invention, a crystalline maltitol powder that has a moisture content of 0.2% or less by weight and 98% or higher maltitol purity per solid content measured by high-performance liquid chromatography has an excellent property still further less prone to consolidation for a delivery or storage period.

Under the same conditions other than particle diameters, powders having a large particle diameter are generally relatively less prone to consolidation, while powders having fine particles are prone to consolidation. Moreover, powders having a wide range of particle diameter distribution are prone to consolidation, while powders having a narrow range of particle diameter distribution are less prone to consolidation.

In a preferred embodiment of the present invention, 90% or more of the crystalline maltitol powder is a powder that has passed through a JIS standard sieve with a mesh size of 0.50 mm (JIS Z8801, which corresponds to a 32-mesh Tyler screen), in light of such tendency. Even when powder particles having such small particle diameters are gathered, the crystalline maltitol powder less prone to consolidation shows excellent physical properties having a score of 0.6 or lower, preferably 0.4 or lower, more preferably 0.2 or lower, particularly preferably 0, in the degree of consolidation. Therefore, it has a low degree of consolidation in which it endures normal delivery or storage conditions more highly than conventional products.

Hereinafter, the crystalline maltitol powder less prone to consolidation of the present invention and the production thereof will be described in detail with reference to Examples. However, the technical scope of the present invention is not limited to the scope described in the Examples.

EXAMPLES

Preparation Example 1

Preparation Example of Crystalline Maltitol Powder Less Prone to Consolidation of the Present Invention A crystalline maltitol powder less prone to consolidation (Sample 1) of the present invention was obtained by charging 2.0 kg of commercially available crystalline maltitol powder (manufactured by Towa Chemical Industry Co., Ltd., trade name LESYS (registered trademark), lot no. 304127) (moisture content: 0.09% by weight, maltitol purity: 99.7%, 99.5% of the powder has passed through a JIS sieve with a mesh size of 0.50 mm) into a cylindrical container of 65 mm in inside diameter and 1000 mm in height having a capacity of approximately 3 liters and subjecting the container to a treatment wherein an air adjusted to a temperature of 30 to 33° C. and a relative humidity of 5% was allowed to pass through the container at SV (space velocity)=11.1 for 24 hours. The obtained product (Sample 1) of the present invention had a score of 0 in a consolidation test result by the present assay method of degree of consolidation and was therefore a crystalline maltitol powder having a property less prone to consolidation.

Preparation Example 2

Preparation Example of Crystalline Maltitol Powder Less Prone to Consolidation of the Present Invention A crystalline maltitol powder less prone to consolidation (Sample 2) of the present invention was obtained by charging 2.0 kg of commercially available crystalline maltitol powder (manufactured by Towa Chemical Industry Co., Ltd., trade name LESYS (registered trademark), lot no. 304167) (moisture content: 0.10% by weight, maltitol purity: 99.7%, 99.82% of the powder has passed through a JIS sieve with a mesh size of 0.50 mm) into the same container as in Preparation Example 1 and subjecting the container to a treatment wherein an air adjusted to a temperature of 30 to 33° C. and a relative humidity of 45% was allowed to pass through the container at SV (space velocity)= 11.1 for 10 hours. The obtained product (Sample 2) of the present invention had a score of 0.2 in a consolidation test result by the present assay method of degree of consolidation and was therefore a crystalline maltitol powder having a property less prone to consolidation.

Preparation Example 3

Preparation Example of Crystalline Maltitol Powder Less Prone to Consolidation of the Present Invention A crystalline maltitol powder less prone to consolidation (Sample 3) of the present invention was obtained by charging 2.0 kg of commercially available crystalline maltitol powder (manufactured by Towa Chemical Industry Co., Ltd., trade name LESYS (registered trademark), lot no. 304127) (moisture content: 0.09% by weight, maltitol purity: 99.7%, 99.5% of the powder has passed through a JIS sieve with a mesh size of 0.50 mm) into the same container as in Preparation Example 1 and subjecting the container to a treatment wherein an air adjusted to a temperature of 25 to 28° C. and a relative humidity of 15% was allowed to pass through the container at SV (space velocity)=10.5 for 20 hours. The obtained product (Sample 3) of the present invention had a score of 0.2 in a consolidation test result by the present assay method of degree of consolidation and was therefore a crystalline maltitol powder having a property less prone to consolidation.

Preparation Example 4

Preparation Example of Crystalline Maltitol Powder Less Prone to Consolidation of the Present Invention A crystalline maltitol powder less prone to consolidation (Sample 4) of the present invention was obtained by charging 2.0 kg of commercially available crystalline maltitol powder (manufactured by Towa Chemical Industry Co., Ltd., trade name. LESYS (registered trademark), lot no. 304167) (moisture content: 0.10% by weight, maltitol purity: 99.7%, 99.82% of the powder has passed through a JIS sieve with a mesh size of 0.50 mm) into the same container as in Preparation Example 1 and subjecting the container to a treatment wherein an air adjusted to a temperature of 40 to 42° C. and a relative humidity of 35% was allowed to pass through the container at SV (space velocity) =14.1 for 15 hours. The obtained product (Sample 4) of the present invention had a score of 0.2 in a consolidation test result by the present assay method of degree of consolidation and was therefore a crystalline maltitol powder having a property less prone to consolidation.

Preparation Example 5

Preparation Example of Crystalline Maltitol Powder Less Prone to Consolidation of the Present Invention A crystalline maltitol powder less prone to consolidation (Sample 5) of the present invention was obtained by charging 2.0 kg of commercially available crystalline maltitol powder (manufactured by Towa Chemical Industry Co., Ltd., trade name LESYS (registered trademark), lot no. 304127) (moisture content: 0.09% by weight, maltitol purity: 99.7%, 99.5% of the powder has passed through a JIS sieve with a mesh size of 0.50 mm) into the same container as in Preparation Example 1 and subjecting the container to a treatment wherein an air adjusted to a temperature of 28 to 30° C. and a relative humidity of 25% was allowed to pass through the container at SV (space velocity)=10.7 for 8 hours. The obtained product (Sample 5) of the present invention had a score of 0.4 in a consolidation test result by the present assay method of degree of consolidation and was therefore a crystalline maltitol powder having a property less prone to consolidation.

Preparation Example 6

Preparation Example of Crystalline Maltitol Powder Less Prone to Consolidation of the Present Invention A crystalline maltitol powder less prone to consolidation (Sample 6) of the present invention was obtained by charging 2.0 kg of commercially available crystalline maltitol powder (manufactured by Towa Chemical Industry Co., Ltd., trade name LESYS (registered trademark), lot no. 304167) (moisture content: 0.10% by weight, maltitol purity: 99.7%, 99.82% of the powder has passed through a JIS sieve with a mesh size of 0.50 mm) into the same container as in Preparation Example 1 and subjecting the container to a treatment wherein an air adjusted to a temperature of 30 to 33° C. and a relative humidity of 8% was allowed to pass through the container at SV (space velocity)= 3 for 48 hours. The obtained product (Sample 6) of the present invention had a score of 0.2 in a consolidation test result by the present assay method of degree of consolidation and was therefore a crystalline maltitol powder having a property less prone to consolidation.

(Comparative Test 1) Test for Measuring Degree of Consolidation

The Samples 1 and 2 obtained in Preparation Examples 1 and 2 and commercially available crystalline maltitol powders shown in Table 1 were used as a sample (the number of each sample n=5). 50 g of each sample crystalline maltitol powder was charged into a sample bottle manufactured by Uezono Youki Co., Ltd. (150 ml in maximum capacity, 4.1 cm in mouth inside diameter, 5.5 cm in shell diameter, and 9.5 cm in overall height) under an environment having a relative humidity of 50% and a temperature of 20° C., and the bottle was tightly stoppered with accompanying polyethylene inner and polypropylene outer lids and a vinyl tape (19-mm-wide vinyl chloride Eslon tape manufactured by Sekisui Chemical Co., Ltd.) is further provided thereon to seal the boundary between the lids and the bottle.

Next, the sealed bottle was charged into a chamber equipped with a temperature control (manufactured by TOKYO RIKAGAKU CO., LTD., EYELA Low Temp Incubator, LTI-1001ED), the degree of consolidation was measured by a test of degree of consolidation described in the present assay method of degree of consolidation after a lapse of 20 days of storage at a temperature of 20° C. and at a temperature of 40° C. alternately repeated at intervals of 12 hours.

The name of each sample used in the test, maltitol purity (%), lot no., moisture content (% by weight), and the proportion of a powder that has passed through the JIS sieve with a mesh size of 0.50 mm are shown in Table 1. The results of the test for evaluating degree of consolidation are shown in Table 2.

TABLE 2

| Group | Sample | Test results | | | | | Average score (degree of consolidation) |
|---|---|---|---|---|---|---|---|
| | | 1st | 2nd | 3rd | 4th | 5th | |
| Invention group | Sample 1 | 0 | 0 | 0 | 0 | 0 | 0.0 |
| | Sample 2 | 0 | 0 | 1 | 0 | 0 | 0.2 |
| | Sample 3 | 0 | 0 | 1 | 0 | 0 | 0.2 |
| | Sample 4 | 0 | 0 | 0 | 1 | 0 | 0.2 |
| | Sample 5 | 0 | 1 | 0 | 0 | 1 | 0.4 |
| | Sample 6 | 0 | 0 | 1 | 0 | 0 | 0.2 |
| Control group | Conventional product 1 | 1 | 1 | 1 | 1 | 1 | 1.0 |
| | Conventional product 2 | 1 | 1 | 1 | 1 | 1 | 1.0 |
| | Conventional product 3 | 1 | 1 | 2 | 1 | 2 | 1.4 |
| | Conventional product 4 | 1 | 1 | 1 | 1 | 2 | 1.2 |
| | Conventional product 5 | 1 | 1 | 2 | 1 | 1 | 1.2 |
| | Conventional product 6 | 1 | 1 | 1 | 1 | 1 | 1.0 |

These test results showed that the products of the present invention show degree of consolidation having a score of 0.2 or lower even in a severe test by the present assay method of degree of consolidation, are less prone to consolidation even during storage or delivery, and have stable powder properties for a long period. Thus, the products of the present invention have an excellent property less prone to consolidation, as compared with commercially available conventional products that show a score of 1.0 or higher in the test results.

TABLE 1

| Group | Name *1 | Sample | Maltitol purity *2 | Lot no. | Moisture content *3 | Proportion of powder that has passed through a JIS sieve with mesh size of 0.50 mm *4 |
|---|---|---|---|---|---|---|
| Invention group | Product of the present invention | Samples 1, 3, 5 | 99.7 | 304127 | 0.09 | 99.50% |
| | Production of the present invention | Samples 2, 4, 6 | 99.7 | 304167 | 0.10 | 99.82% |
| Control group | Conventional product 1 | LESYS | 99.7 | 306117 | 0.10 | 98.95% |
| | Conventional product 2 | LESYS | 99.7 | 304248 | 0.13 | 97.59% |
| | Conventional product 3 | LESYS | 99.6 | 305278 | 0.13 | 98.60% |
| | Conventional product 4 | MALTISORB | 99.8 | E275S | 0.09 | 99.66% |
| | Conventional product 5 | MALTISORB | 99.8 | E353S | 0.12 | 97.30% |
| | Conventional product 6 | MALTISORB | 99.8 | E363S | 0.09 | 98.80% |

Note)
*1: LESYS is a registered trademark of crystalline maltitol manufactured by Towa Chemical Industry Co., Ltd., and MALTISORB is a registered trademark of crystalline maltitol manufactured by Roquette Freres.
*2: In a maltitol purity measurement, high-performance liquid chromatography with an MCI-GEL CK08EC column was used, under conditions of temperature: 85° C., eluent: water, elution rate: 0.5 ml/min., and detector: differential refractometer (RI).
*3: In a moisture content measurement, computrac MAX2000 Moisture Analyzer manufactured by Arizona Instrument was used. The measurement was terminated with respect to the point in time when the change of 0.008%/min. at the ratio was not observed for 5 g ± 1 g of the sample at a temperature of 80° C.
*4: The proportion of a powder that has passed through the JIS sieve with a mesh size of 0.50 mm was measured by charging 5 to 7 g of the sample into SEISHIN ROBOT SIFTER RPS-85 manufactured by SEISHIN ENTERPRISE CO., LTD., to which a 32-, 60-, 80-, 100-, 150-, and 200- mesh sieve was attached, and adopting measurement conditions of oscillation time: 5 minutes, vibration level: 2, and pulse interval: 1 second.

(Comparative Test 2) Test for Measuring Degree of Consolidation

The Samples 1 to 6 obtained in Preparation Examples 1 to 6, commercially available crystalline sorbitol powders and crystalline xylitol powders shown in Table 3, were treated in the same way as in Preparation Example 2, and used as a sample. Each sample (n=5) charged into a sample bottle manufactured by Uezono Youki Co., Ltd. was charged into a chamber equipped with a temperature control in the same way as in Comparative Test 1. The degree of consolidation was measured by the same test of degree of consolidation as in Comparative Test 1 after a lapse of 20 days of storage at a temperature of 20° C. and 40° C. alternately repeated at intervals of 12 hours.

The name of each sample used in the test, purity (%), lot no., moisture content (% by weight), and the proportion of a powder that has passed through the JIS sieve with a mesh size of 0.50 mm are shown in Table 3. The same moisture content measurement method as that for maltitol was adopted for xylitol and sorbitol, and a quantification method described in Japan's Specifications and Standards for Food Additives (1999) was adopted as a purity measurement method for each of xylitol and sorbitol. The results of the test for evaluating degree of consolidation for the samples described in Table 3 are shown in Table 4.

xylitol powder manufactured by Yucheng Futian Pharmacy Co., Ltd.; and Neosorb (Samples 13 and 14) is a crystalline sorbitol powder manufactured by Roquette Freres.

TABLE 4

| Group | Sample | Test results | | | | | Average score (degree of consolidation) |
|---|---|---|---|---|---|---|---|
| | | 1st | 2nd | 3rd | 4th | 5th | |
| Invention group | Sample 1 | 0 | 0 | 0 | 0 | 0 | 0.0 |
| | Sample 2 | 0 | 0 | 1 | 0 | 0 | 0.2 |
| | Sample 3 | 0 | 0 | 1 | 0 | 0 | 0.2 |
| | Sample 4 | 0 | 0 | 0 | 1 | 0 | 0.2 |
| | Sample 5 | 0 | 1 | 0 | 0 | 1 | 0.4 |
| | Sample 6 | 0 | 0 | 1 | 0 | 0 | 0.2 |
| Control group | Sample 7 | 2 | 2 | 2 | 2 | 2 | 2.0 |
| | Sample 8 | 2 | 2 | 2 | 2 | 2 | 2.0 |
| | Sample 9 | 2 | 2 | 2 | 2 | 2 | 2.0 |
| | Sample 10 | 2 | 2 | 2 | 2 | 2 | 2.0 |
| | Sample 11 | 2 | 2 | 2 | 2 | 2 | 2.0 |
| | Sample 12 | 2 | 2 | 2 | 2 | 2 | 2.0 |
| | Sample 13 | 2 | 2 | 1 | 2 | 2 | 1.8 |
| | Sample 14 | 2 | 2 | 2 | 2 | 1 | 1.8 |

These test results showed that sorbitol and xylitol, which are also sugar alcohols as with the products of the present

TABLE 3

| Group | Name *1 | Sample | Purity | Lot no. | Moisture content | Proportion of powder that has passed through JIS sieve with mesh size of 0.50 mm |
|---|---|---|---|---|---|---|
| Invention group | Product of the present invention | Samples 1, 3, 5 | 99.7 | 304127 | 0.09 | 99.50% |
| | Product of the present invention | Samples 2, 4, 6 | 99.7 | 304167 | 0.10 | 99.82% |
| Control group | Sample 7 | Xylit (product of Japanese Pharmacopoeia) | 99.9 | 404068 | 0.09 | — |
| | Sample 8 | Xylit | 99.9 | 404196 | 0.11 | — |
| | Sample 9 | Sorbit LTS-P20 | 98.9 | 1703421 | 0.26 | — |
| | Sample 10 | Sorbit LTS-P50 | 99.0 | 1703451 | 0.28 | — |
| | Sample 11 | Xylitol | 99.7 | H125T3B15 | 0.10 | — |
| | Sample 12 | Xylitol | 99.8 | 0307110 | 0.09 | — |
| | Sample 13 | Neosorb | 98.9 | E23B | 0.41 | — |
| | Sample 14 | Neosorb | 99.1 | E873Z | 0.42 | — |

Note)
*1: in the description of the name section of each sample in the table, the Samples 1 and 2 are the same as in Table 1; Xylit (Samples 7 and 8) is a commercially available crystalline xylitol powder (all particles of 1.99 mm or less in particle diameter) manufactured by Towa Chemical Industry Co., Ltd.; Sorbit (Samples 8 and 10) is a commercially available crystalline sorbitol powder (Sorbit LTS-P20: 1.18 mm to 0.406 mm in particle diameter, Sorbit LTS-P50: all particles of 0.406 mm or less in particle diameter) manufactured by Towa Chemical Industry Co., Ltd.; xylitol (Sample 11) is a crystalline xylitol powder manufactured by Danisco Cultor America; xylitol (Sample 12) is a crystalline xylitol powder manufactured by Yucheng Futian Pharmacy Co., Ltd.; and Neosorb (Samples 13 and 14) is a crystalline sorbitol powder manufactured by Roquette Freres.

Note) *1: in the description of the name section of each sample in the table, the Samples 1 and 2 are the same as in Table 1; Xylit (Samples 7 and 8) is a commercially available crystalline xylitol powder (all particles of 1.99 mm or less in particle diameter) manufactured by Towa Chemical Industry Co., Ltd.; Sorbit (Samples 8 and 10) is a commercially available crystalline sorbitol powder (Sorbit LTS-P20: 1.18 mm to 0.406 mm in particle diameter, Sorbit LTS-P50: all particles of 0.406 mm or less in particle diameter) manufactured by Towa Chemical Industry Co., Ltd.; xylitol (Sample 11) is a crystalline xylitol powder manufactured by Danisco Cultor America; xylitol (Sample 12) is a crystalline invention, do not produce an effect as shown by the product of the present invention and are consolidated when treated in the same way.

the invention claimed is:

1. A method for producing a crystalline maltitol powder less prone to consolidation, comprising the steps of bringing an air having a temperature of 20 to 50° C. and a relative humidity of 5 to 50% into contact at a space velocity [=SV] of 2 to 15($h^{-1}$) for 5 to 50 hours with a crystalline maltitol powder having a score exceeding 0.6 in degree of consolidation measured by an assay method of degree of consolidation, thereby converting the crystalline maltitol powder to a crystalline maltitol powder having a score of 0.6 or lower in the degree of consolidation wherein in said assay method of degree of consolidation 50 g of a sample crystalline maltitol powder is charged into a commercially available sample bottle with 150 ml in maximum capacity, 4.1 cm in mouth inside diameter, 5.5 cm in shell diameter, and 9.5 cm in overall height under an environment having a relative humidity of 50% and a temperature of 20°C.

wherein the bottle is tightly stoppered with accompanying polyethylene inner and polypropylene outer lids, and a vinyl tape is further provided thereon to seal the boundary between the lids and the bottle, wherein the sealed bottle is charged into a chamber equipped with a temperature control and evaluated according to the following judgment criteria (1) to (3) after a lapse of 20 days of storage at a temperature of 20° C. and 40° C. alternately repeated at intervals of 12 hours, wherein the evaluation is performed with five identical samples, and an average value of test results of these five samples is used as the degree of consolidation in the present assay method of degree of consolidation, wherein (1) a score of 0 is given when the sample powder wholly flows toward the bottle mouth and thereby exhibits flowability without attaching onto the inside bottom of the sample bottle or slightly attaches onto the inside bottom of the sample bottle but flows toward the bottle mouth and thereby exhibits flowability, on the way of tilting the sample bottle containing the sample at an angle of 90 degrees without giving an impact thereto;

(2) a score of 1 is given when the sample powder neither flows nor shows flowability by tilting the sample bottle at an angle of 90 degrees but flows toward the bottle mouth on the way of or within 1 minute after further tilting the bottle at an angle of 180 degrees; and (3) a score of 2 is given when the sample powder does not flow toward the bottle mouth even after a lapse of 1 minute after tilting the sample bottle at an angle of 180degrees.

2. The method for producing a crystalline maltitol powder less prone to consolidation according to claim 1, comprising the steps of bringing an air having a temperature of 25 to 42° C. and a relative humidity of 8 to 45% into contact at a space velocity [=S V] of 3 to 14 ($h^{-1}$) for 8 to 48 hours with a crystalline maltitol powder having a score exceeding 0.6 in degree of consolidation measured by the assay method of degree of consolidation, and thereby converting the crystalline maltitol powder to a crystalline maltitol powder having a score of 0.6 or lower in the degree of consolidation.

3. The method for producing a crystalline maltitol powder less prone to consolidation according to claim 1, wherein the air brought into contact has a temperature of 28 to 33° C., and thereby converting the crystalline maltitol powder to a crystalline maltitol powder having a score of 0.4 or lower in the degree of consolidation measured by the assay method of degree of consolidation.

4. The method for producing a crystalline maltitol powder less prone to consolidation according to claim 1, wherein the converted crystalline maltitol powder has a score of 0.2 or lower in the degree of consolidation measured by the assay method of degree of consolidation.

5. The method for producing a crystalline maltitol powder less prone to consolidation according to claim 1, wherein the crystalline maltitol powder having a score of 0.6 or lower in the degree of consolidation measured by the assay method of degree of consolidation has a moisture content of 0.2% or less by weight and a maltitol content of 98% or more by weight per solid content.

6. The method for producing a crystalline maltitol powder less prone to consolidation according to claim 1, wherein 90% or more by weight of the crystalline maltitol powder having a score of 0.6 or lower in the degree of consolidation measured by the assay method of degree of consolidation is a powder that has passed through of a JIS sieve with a mesh size of 0.50 mm.

* * * * *